United States Patent [19]

Cayer et al.

[11] Patent Number: 5,597,777
[45] Date of Patent: Jan. 28, 1997

[54] OXYFLUORFEN DISPERSIBLE GRANULE FORMULATION

[75] Inventors: Christine M. Cayer, Wyncote; Vincent A. Musco, Southampton; Robert F. Peterson, Jr., New Hope, all of Pa.

[73] Assignee: Rohm and Haas Company, Philadelphia, Pa.

[21] Appl. No.: 263,118

[22] Filed: Jun. 10, 1994

Related U.S. Application Data

[63] Continuation of Ser. No. 667,136, Mar. 11, 1991, abandoned.

[51] Int. Cl.$^6$ .......................... A01N 25/32; A01N 31/14
[52] U.S. Cl. ................................ 504/116; 504/352
[58] Field of Search ........................ 504/116, 352

[56] References Cited

U.S. PATENT DOCUMENTS

| | | | |
|---|---|---|---|
| 3,617,246 | 11/1971 | Duyijes et al. | 71/79 |
| 3,920,442 | 11/1975 | Albert et al. | 71/92 |
| 4,185,995 | 1/1980 | Bayer et al. | 71/124 |

FOREIGN PATENT DOCUMENTS

| | | |
|---|---|---|
| 252896 | 1/1988 | European Pat. Off. . |
| 1433882 | 1/1973 | United Kingdom . |

OTHER PUBLICATIONS

The Agrochemicals Handbook, Douglas Hartley, Ed., The Royal Society of Chemistry, 1987.

*Primary Examiner*—Allen J. Robinson
*Assistant Examiner*—Brian Bembenick
*Attorney, Agent, or Firm*—Joseph F. Leightner

[57] ABSTRACT

A dispersible granular formulation has been developed which contains oxyfluorfen herbicide. This formulation provides excellent suspensibility characteristics, and reduces post-emergent vapor phytotoxicity.

21 Claims, No Drawings

OXYFLUORFEN DISPERSIBLE GRANULE FORMULATION

This application is a continuation of application Ser. No. 667,136 filed Mar. 11, 1991 (abandoned).

BACKGROUND OF THE INVENTION

This invention relates to novel dispersible granule formulations of the herbicide oxyfluorfen and processes for their preparation.

Water dispersible granular pesticide formulations are known. These formulations are desirable because they avoid the use of potentially toxic solvents and permit the use of easily-disposable paper containers or water soluble containers. Potential exposure of pesticide applicators and the general public to the pesticide or solvent is thereby reduced.

Typical dispersible granular pesticide formulations are described for example in GB 1,433,882, EP 0,252,896 and U.S. Pat. No. 3,920,442. GB 1,433,882 describes a process for preparing dispersible granules by blending premilled, water-insoluble active ingredient, dispersing agents, disintegrating agents and wetting agents in an aqueous suspension. The aqueous mix is extruded to form granules which are then dried to yield the final product. U.S. Pat. No. 3,920,442 describes water dispersible pesticide aggregates containing 5 to 95% by weight of pesticide. The aggregates are prepared by contacting the finely divided solid ingredients in a fluidized bed with a fine spray of water or a solution of the binder-dispersant followed by drying.

In attempts at making pesticide granules, it has often been found that granules or agglomerates prepared from the formulated wettable powders of the art using well-known agglomerating techniques and using water as the agglomerating agent, are not easily dispersible in water. On the other hand, agglomerates which are readily water-dispersible are often not sufficiently resistant to attrition and form a fine dust fraction upon handling and shipping. If conventional binders are added to make the granules strong, then they are not dispersible in water. Techniques such as tabletting, extrusion and rolling which involve high-pressure compaction of moistened mixtures containing finely divided pesticides, diluents, binder and dispersant, as described in U.S. Pat. No. 3,617,246, lead to dense pellets, tablets, plates, and rods which are subsequently dried and crushed. These latter techniques have also been used to form granules containing up to 50% of active pesticide, but the resulting granules are not rapidly or completely water dispersible and are not suitable for use in preparing sprayable suspensions.

Low-melting solids such as oxyfluorfen present an especially difficult problem in the preparation of a dispersible granule formulation. The low-melting solid, herein defined as melting below 100° C., tends to melt or become sticky during or subsequent to the grinding process which is a necessary step in preparing dispersible granules. EP 0,252,896 describes a possible solution to this problem which requires micro-encapsulation of low-melting pesticides prior to granulation. However, microencapsulation involves additional processing steps and adds to the cost of the overall formulation.

In the case of the herbicide oxyfluorfen, it has not heretofore been possible to produce a dispersible granular product which combines the features of a high active ingredient content, good suspensibility and dispersion properties as well as resistance to attrition thereby avoiding the formation of a dust.

Conventional oxyfluorfen formulations also suffer from the loss of herbicide vapor from the site of application which is undesirable because of reduction of herbicide in the soil and possible vapor injury to the growing crops in or near the location to which the herbicide is applied.

Oxyfluorfen is known to cause injury to soybeans by volatization under field conditions. Grabowski and Hopen, *Weed Science* 1985, Vol. 33, pg. 306–309 show that emulsifiable concentrate, wettable powder and soil applied granular formulations of oxyfluorfen cause vapor injury to plants under greenhouse conditions.

SUMMARY OF THE INVENTION

This invention relates to dispersible granule formulations of oxyfluorfen herbicide and processes for preparing these formulations including pan granulation or extrusion of a pre-wet mixture comprising finely-ground active ingredient, surfactant and optionally wetting agent, dispersing agent and carrier. The dispersible granules produced by these processes provide good suspensibility and also significantly reduce post-emergent oxyfluorfen vapor injury to plants as compared to emulsifiable concentrate and wettable powder formulations without reducing pre-emergent herbicide activity.

DETAILED DESCRIPTION OF THE INVENTION

According to this invention, there is provided a composition, in granular form, comprising oxyfluorfen and optionally one or more surfactants which significantly reduces vapor phase injury to growing plants.

By granular form, we mean granules substantially all of which have a mean particle size of at least 0.1 mm., which is a particle size much larger than the mean particle size of a powder, the mean particle size of which is measured in microns.

Oxyfluorfen is 2-chloro-1-(3-ethoxy-4-nitrophenoxy)-4-(trifluoromethyl)benzene. Dispersible granular, also known as dry flowable, formulations are designated in agricultural literature as DG, DF or WG. The percentage active ingredient in the formulation is sometimes indicated, as for example, oxyfluorfen 80 DG or oxyfluorfen 60 DF.

A dispersible granular herbicide composition designed for dispersion in a liquid carrier should ideally have a high content of active material, should be readily dispersible in the carrier and should then form a dispersion which is as stable as possible, requiring the minimum of subsequent agitation for homogeneity. The liquid carrier will, of course, for convenience normally be water. We have now devised a way to make granules containing from about 10% to about 90% oxyfluorfen which readily break down when they are stirred into a liquid carrier to give a stable dispersion of the active ingredient.

This invention is a dispersible granule comprising oxyfluorfen having a suspensibility of at least about 70%. It has been found that this dispersible granule formulation causes significantly less vapor injury to growing plants compared to emulsifiable concentrate and wettable powder formulations of oxyfluorfen without reducing preemergent herbicide activity.

In this specification "significantly less vapor injury" means at least a 30% reduction in injury by the dispersible granules of this invention compared to conventional formulations in an assay equivalent to the vapor bioassay described in Example 12.

In addition to the active ingredient, oxyfluorfen, the mixture to be formed into dispersible granules will contain one or more surfactants and, optionally, flow aids, dispersants, disintegrants, wetting agents and defoaming agents.

The suspensibility test is determined in accordance with a variation of the procedure of the Collaborative International Pesticides Analytical Council (CIPAC) Handbook, Vol. 1, Ed. G. R. Raw (1970), Method Number MT 15.1. Standard hard water (342 ppm as calcium carbonate) was prepared according to CIPAC method MT 18.1.4., also known as Army Hard Water. The suspensibility test is further described in Example 1.

The term "surfactant" is used in the broad sense to include materials which may be referred to as emulsifying agents, dispersing agents and wetting agents, and the surfactant component may comprise one or more surfactants selected from the anionic, cationic and nonionic types.

Examples of surfactants of the anionic type include soaps, salts of aliphatic monoesters of sulfuric acid such as sodium lauryl sulfate, salts of sulfonated aromatic compounds, for example sodium dodecylbenzene sulfonate, sodium or ammonium lignosulfonate or butylnaphthalene sulfonate, and a mixture of the sodium salts of diisopropyl- and triiso-propylnaphthalene sulfonates. Suitable agents of the non-ionic type include, for example, the condensation products of ethylene oxide with fatty alcohols such as oleoyl alcohol or cetyl alcohol, or with alkyl phenols such as octyl phenol, nonyl phenol and octyl cresol. Other non-ionic agents are the partial esters with ethylene oxide and the lecithins.

Preferably the surfactant component will comprise at least one wetting agent such as those selected from alkyl naphthalene sulfonates, alkylaryl polyoxyethylene ammonium sulfonates, sulfosuccinates and nonionics such as tridecyl alcohol ethoxylate; or at least one dispersing agent such as those selected from the group of naphthalene sulfonates, lignosulfonates and polyacrylates.

Typically the total surfactant component will comprise from 0.1 to 25% and preferably from 1 to 15% by weight of the dry weight of the composition.

In the context of this specification, a dispersing agent is a surfactant which facilitates the dispersion of the pesticide particles when the product is added to a liquid, for example water. The dispersing agents used are preferably water-soluble ones. Phosphate esters, polycarbonate/acrylates and calcium lignosulfonates produced granules with poor suspensibility. Examples of dispersants preferred for the dispersible granule formulations of this invention include: Polyfon® H, Polyfon O, Reax® 88B, Morwet® D-425, Reax 45A, Polyfon T, Polyfon F, Lignosol™ XD-65, Reax 45L, Reax 85A, Reax 910, Polyfon OD, PC-825, described in Table 1. Most preferred dispersants are: Reax® 85A, Polyfon® H and Morwet® D425.

Examples of surfactants preferred as wetting agents for the dispersible granule formulations of this invention include Morwet® B, Morwet EFW, Sellogen® DFL, Morwet IP, Igepon® AC-78, Igepon T-77, Aerosol OT-B, and Triton® XN-45S, described in Table 1. Most preferred wetting agents are Morwet B and Triton XN-45S.

All surfactants act as dispersing agents in some degree, and also in some degree as wetting agents; most surface-active agents are however, more efficient in one capacity than the other. The worker of ordinary skill in the formulation art can select a surfactant most suitable for the purpose in view.

Small particles of a low-melting solid such as oxyfluorfen often tend to stick together thereby causing flow problems in processing the material. Flow enchancing agents also called flow aids such as clays or silica particles may be used to minimize these problems. Flow aids preferred for the oxyfluorfen dispersible granular include HiSil® 233, Wessalon® 50S, Cab-O-Sil® M-5, Wessalon S, Barden® Clay, and Microcel® E. Most preferred is HiSil 233, a silicate flow aid. The flow aid content of the dispersible granule may vary from 0 to 90% and preferably from 1 to 8%.

Addition of a silicon containing antifoaming agent is desirable to aid in the processing and use of oxyfluorfen dispersible granules. Defoaming agents may be used in amounts of 0.1% to 5%; a preferred range is about 0.2% to 1.0%. The preferred defoaming agent is Mazu DF-1300.

Disintegrants, which are water soluble organic compounds such as starch or sugar or water soluble inorganic salts such as sodium acetate or sodium bicarbonate, are sometimes used in dispersible granule formulations. See GB 1,433,882 for example. We have found that certain disintegrants have different effects on the oxyfluorfen dispersible granules of this invention; formulations containing sodium bicarbonate were found to disperse less effectively. On the other hand, Primojel® disintegrant, a sodium starch glycolate provided a dispersible granule with good physical properties and biological activity.

This invention comprises a dispersible granule containing by weight percent: oxyfluorfen, 10–90%; dispersent 0–25%; wetting agent 0–25%; disintegrant 0–5%; flow aid 0–90%; and defoaming agent 0–5%.

The most preferred composition of this invention comprises by weight percent: oxyfluorfen 80.4%; dispersant, Reax 85A, 17.5%; flow aid, HiSil 233, 1.6%; defoaming agent, Mazu DF-1300, 0.5%; and water, less than 1%.

Examples of dispersant, wetting agents, flow aids and defoaming agents useful in this invention are shown in Table I.

TABLE 1

| | Producer | Chemical Type |
|---|---|---|
| Dispersants | | |
| Polyfon ® H | Westvaco Chemicals | Aliphatic and aromatic |
| Polyfon F | P.O. Box 70848 | sulfonated lignin |
| Polyfon O | Charleston Hts., SC | |
| Polyfon OD | 29415-0848 | |
| Reax ® 88B | | |
| Reax 45A | | |
| Reax 45L | | |
| Reax 85A | | |
| Reax 910 | | |
| Reax 80C | | |
| Reax 83A | | |
| Reax 100M | | |
| PC-876A | | Ammonium lignosulfonate |
| Lignosol ® XD-65 | Reed Lignin, Inc. 81 Holly Hill Lane Greenwich, CT 06830 | Sodium lignosulfonate |
| Orzan ® A | ITT Rayonier Inc. 18000 Pacific Highway S. Suite 900 Seattle, WA 98188 | Ammonium lignosulfonate |
| Wetting Agents | | |
| Morwet ® B | DeSoto, Inc. 2001 N. Grove Fort Worth, TX 76113 | Sodium n-butyl naphthalene sulfonate |

TABLE 1-continued

| | Producer | Chemical Type |
|---|---|---|
| Morwet EFW | | Napthalene sulfonate |
| Morwet D425 | | Naphthalene sulfonate |
| Morwet IP | | Sodium diisopropyl naphthalene sulfonate |
| Sellogen® DFL | Henkel Corp. Emery Group 11 501 Northlake Drive Cincinnati, OH 45249 | Alkyl naphthalene sulfonate |
| Igepon® AC-78 | GAF Corp. 140 W. 51st. St. New York, NY 10020 | Sodium cocyl isethionate |
| Igepon T-77 | | Sodium methyl oleoyl taurate |
| Aerosol® OT-B | American Cyanamid One Cyanamid Plaza Wayne, NJ 07470 | Sodium dioctyl sulfo succinate |
| Triton® XN-45S | Union Carbide Co. Industrial Chem. Div. 39 Old Ridgebury Rd. Danbury, CT 06817 | Ammonium alkyl/aryl polyoxyethylene sulfate |
| Flow Aids | | |
| HiSil® 233 | PPG Industries One Gateway Center Pittsburgh, PA 15222 | Silica |
| Wessalon® 505 | Degussa Corp. Rt. 46, Hollister Rd. Teterboro, NJ 07608 | Silica |
| Wessalon S | | Silica |
| Cab-O-Sil® M-5 | Cabot Corp. Boston, MA 02110 | Silica |
| Barden® Clay | J. M. Huber Corp. Rt. #4 Macon, GA 30201 | Clay |
| Microcel® E | Johns-Manville P.O. Box 5108 Denver, CO 80217 | Silicate |
| Defoaming Agents | | |
| Mazu® DF 1300 | Mazer Chemicals 3938 Poreti Drive Gurnee, IL 60031 | Silicone and Silica |

The dispersible granules of this invention are prepared by milling oxyfluorfen, optionally with flow aid to a particle size of less than 20 microns preferably less than 10 microns and more preferably less than 5 microns; then adding a dispersant, water and optionally a wetting agent and a defoaming agent and mixing until a paste is obtained; agglomerating the paste; and drying the granules thus produced.

Agglomeration or granulation may be accomplished by any operable means such as wet granulation, tabletting, pan agglomeration, fluid bed agglomeration or extrusion. Extrusion is the preferred method.

The preferred amount of water to be added to the mixture to be agglomerated is 18 to 25 parts per 100 parts by weight.

After extrusion, the dispersible granules are dried. For storage stability, it is preferred to reduce the residual water to at least 2% and preferably below 1% by weight. Drying temperatures above about 100° C. are injurious to the product. The preferred drying temperature is less than about 60° C. and more preferably less than about 50° C. Drying may be accomplished by any suitable drying means preferably one which supplies inert gas at a controlled temperature. A two stage fluid bed dryer is preferred.

A preferred process for producing the oxyfluorfen dispersible granules of this invention comprises:

(a) milling a mixture of oxyfluorfen, and flow aid to a particle size between 3 and 15 microns;

(b) adding a surfactant, and 18–25% water (based on the total weight of ingredients) to the milled mixture of step (a) and mixing until a homogeneous, extrudable paste is obtained;

(c) extruding the paste obtained in step (b);

(d) drying the extruded granules at a temperature of less than about 60° C. to a moisture content of less than about 2% by weight.

The following examples describe the preparation of the oxyfluorfen dispersible granules of this invention and are intended only to illustrate the invention and not intended to limit the scope of the invention which is defined by the claims.

EXAMPLE 1

Preparation of Oxyfluorfen 80 DG by Extrusion

Technical oxyfluorfen (97% purity by weight) was melted by heating at 100° C. for 24 hours. The molten material was then poured into aluminum foil lined trays to a depth of about one inch. After cooling at room temperature for 24 hours, the solid was broken up and milled in a coffee mill.

The coarse milled oxyfluorfen was blended with HiSil 233 flow aid in a Marion mixer (manufactured for Rapid Machinery Co., Marion, Iowa by Texas Div. Tranter Inc. Old Burk Road, Wichita Falls, Tex.) in the following ratio of ingredients in parts by weight: oxyfluorfen 80.4; HiSil 1.6 and mixed for 20 minutes.

The above blend was milled in a Bantam micropulverizer, (manufactured by Mikropul, 10 Chantaur Road, Summit, N.J. 07901) fitted with a 0.042 inch screen and automatic feeder. The mean particle size of micropulverized product was about 40 microns.

The micropulverized product was then air milled in an 8" horizontal (pancake) jet mill (manufactured by Fluid Energy Processing and Equipment Co., 153 Penn Energy, Hatfield, Pa. 19440). An Accu-Rate feeder (made by Accu-Rate, 746 E. Milwaukee Street, White Water, Wis. 53190) was fitted with a 2" screw feed nozzle positioned to deliver micropulverized material to the air mill. High pressure nitrogen was used for both feeding and grinding to maintain an oxygen concentration below 10%. The ground material was collected in the air bag. The air mill was operated at a nitrogen feed pressure of 65 psig, a nitrogen grind pressure of 60 psig, and an accurate-rate setting of 100.

Under these conditions the milling rate was 8–10 lbs./hour. The mean particle size was about 5 microns.

The above blend (82.0 parts by weight), Reax 85A dispersant (17.5 parts by weight), Mazu DF 1300 antifoam (0.5 parts by weight) and water (25 parts by weight) were mixed in a Kitchen Aid mixer (made by Hobart, Kitchen Aid Div., Troy, Ohio) for approximately 2 to 3 minutes.

The mixture was transferred to a KAR 130 extruder (made by Tsu Tsui Rikagaku Kikai Co., Ltd., Japan) fitted with a 1.0 mm screen. After extrusion, the extrudate was air dried to a moisture content of 1 to 2% by weight at a temperature of less than 40° C.

Suspensibility (variation of CIPAC method)

Two grams of oxyfluorfen DG was placed in a glass-stoppered graduated cylinder containing 248 ml of Army Hard Water at 25° C. The cylinder was inverted 30 times over a period of 90 seconds and allowed to stand for 30 minutes. The bottom 25 ml was separated, evaporated and dried for 16 hours at 60° C.; and the resulting residue was used to calculate the percent suspensibility by the following formula.

$$\% \text{ suspensibility} = \frac{2 - \text{weight of residue in grams}}{2} \times 111$$

EXAMPLES 2–9

A number of formulations of oxyfluorfen DG were prepared following the general procedure of Example 1 using variations of dispersants, wetting agents, disintegrants, defoaming agents and flow aids. The components and results are shown in Table 2 below.

a greenhouse and watered by subirrigation and overhead. Subsequently, only overhead watering was used.

Test species employed are listed in Tables 3 and 4.

Each formulation to be evaluated was suspended in water and sprayed over the flats or pots using a carrier volume equivalent to 25 gallons per acre at the rate of application in grams per hectare (g/Ha) specified in the tables. About two or three weeks after application of the test formulation, the state of growth of the plants was observed. Each species was evaluated on a scale of 0 to 100 in which 0 equals no control and 100 equals total control of the species.

Tables 3 and 4 show the pre-emergent herbicide activity of the oxyfluorfen dispersible granule formulations of this invention compared with oxyfluorfen emulsifiable concentrate (1.6 E), a commercial formulation of Rohm and Haas Company, Philadelphia, Pa. 19105.

TABLE 2

| Example # | % Oxyfluorfen | Dispersant (%) | Disintegrant (%) | Wetting Agent (%) | Mazu Defoam (%) | Flow aid (%) | Percent Suspensibility |
|---|---|---|---|---|---|---|---|
| 1 | 80.4 | Reax 85A 17.5 | — | — | 0.5 | HiSil 233 1.6 | 90 |
| 2 | 80.4 | Reax 85A 15.5 | — | Triton XN 455 2.0 | 0.5 | HiSil 233 1.6 | 90 |
| 3 | 80.4 | Morwet D425 17.5 | — | — | 0.5 | HiSil 233 1.6 | 86 |
| 4 | 77.9 | Reax 85A 18.0 | Primogel 2.0 | — | 0.5 | HiSil 233 1.6 | 84 |
| 5 | 77.9 | Reax 85A 18.0 | NaHCO$_3$ 2.0 | — | 0.5 | HiSil 233 1.6 | 71 |
| 6 | 77.9 | Reax 85A 21.6 | — | — | 0.5 | — | 95 |
| 7 | 77.9 | PC-876 H 20.0 | — | — | 0.5 | HiSil 233 1.6 | 95 |
| 8 | 83.4 | Reax 85A 15.0 | — | — | — | HiSil 233 1.6 | 89 |
| 9 | 21.0* | Reax 85A 20.0 | — | — | — | HiSil 233, 1.6 Barden Clay 57 | 85 |
| 10 | 77.9 | Reax 85A 20.0 | — | — | 0.5 | HiSil 233 1.6 | 83 |

*75% active ingredient

EXAMPLE 10

Preparation of Oxyfluorfen DG by Granulation

Oxyfluorfen (77.9 parts by weight) and HiSil 233 (1.6 parts by weight) were milled to a particle size of approximately 5 microns. Reax 85A (20.0 parts by weight) and Mazu DF 1300 (0.5 parts by weight) were added to the oxyfluorfen and HiSil and mixed in a Hobart blender until the mixture was well blended.

Water was added slowly to the powder while mixing. When the mixture began to granulate, addition of water was stopped and stirring was continued until granulation was complete.

The resulting granules were dried under vacuum and screened to remove fines and oversized particles.

EXAMPLE 11

Pre-Emergent Herbicide Test Procedure

The following test procedure was employed to assess the herbicidal activity of the formulations of the invention. Seeds of selected plants were planted in flats or pots. The test compound was sprayed directly onto the soil surface immediately after planting. The flats or pots were then placed in

TABLE 3

Pre-emergent Herbicide Test; 300 g/Hectare Active Ingredient

| Formulation | Average Dicot % Control | Average Monocot % Control |
|---|---|---|
| Oxyfluorfen DG Example 1 | 87 | 100 |
| Oxyfluorfen DG Example 2 | 87 | 100 |
| Oxyfluorfen DG Example 3 | 91 | 100 |
| Oxyfluorfen Emulsifiable Concentrate (1.6 E) | 94 | 100 |
| Untreated | 0 | 0 |

Species used in the above test are listed below

| Dicots in Test | | Monocots in Test |
|---|---|---|
| Bidens | *Bidens pilosa* | Barnyardgrass, |
| Morningglory | *Ipomoea lacunosa* | *Echinochloa crus-galli* |
| Nightshade | *Solanum nigrum* | Foxtail *Setaria viridis* |
| Pigweed | *Amaranthus retroflexus* | |
| Smartweed | *Polygonum lapathifolium* | |
| Velvetleaf | *Abutilon theophrasti* | |

TABLE 4

Pre-emergent Herbicide Test; 300 g/Hectare Active Ingredient

| Formulation | Average Dicot % Control | Average Monocot % Control |
|---|---|---|
| Oxyfluorfen DG Example 2 | 88 | 99 |
| Oxyfluorfen DG Example 4 | 91 | 98 |
| Oxyfluorfen DG Example 5 | 93 | 100 |
| Oxyfluorfen Emulsifiable Concentrate (1.6 E) | 86 | 100 |
| Untreated | 0 | 0 |

Species used in the above test are listed below.

| Dicots | | Monocots |
|---|---|---|
| Bidens | *Bidens pilosa* | Barnyardgrass, *Echinochloa crus-galli* |
| Morningglory | *Ipomoea lacunosa* | Foxtail *Setaria viridis* |
| Nightshade | *Solanum nigrum* | |
| Velvetleaf | *Abutilon theophrasti* | |

EXAMPLE 12

Vapor Bioassay

The vapor assay was designed to detect herbicidal injury that can occur only from vaporized herbicides. Unsprayed plants were exposed to potential vapors within an enclosed system as follows.

Typical greenhouse soil (50:50 of soil to Redi Earth®) was added to an eight inch diameter circular pot six inches tall to within one inch of the top and then covered with a 2:1 soil and sand mix. The pot was sprayed with a herbicide in the conventional manner. The sprayed pot was immediately placed in the greenhouse and the soil wetted from the bottom up using a water-filled saucer. After wetting the soil, a 2 inch pot of velvetleaf was placed in a small petri dish in the center of the pot.

After placing the untreated plants on the treated soil, a one gallon clear plastic bag was inverted over the eight inch pot forming a tightly sealed tent over the entire system. The pot/tent system was left in the greenhouse for four days at which time injury evaluations were made using a scale of 0 (no injuries) to 100 (complete kill).

Tables 5 and 6 show the vapor injury caused by dispersible granule formulations of this invention in comparison to the oxyfluorfen emulsifiable concentrate (1.6 E) and oxyflourfen wettable powder (25 WP) commercial formulations of Rohm and Haas Company, Philadelphia, Pa 19105.

TABLE 5

Oxyfluorfen DG Vapor Test
300 g/Hectare Active Ingredient
Velvetleaf
4 Days after Application

| Formulation | % Injury |
|---|---|
| Oxyfluorfen DG Example 1 | 30 |
| Oxyfluorfen DG Example 2 | 25 |
| Oxyfluorfen DG Example 3 | 35 |
| Oxyfluorfen Emulsifiable Concentrate (1.6 E) | 100 |
| Untreated | 0 |

TABLE 6

Oxyfluorfen DG Vapor Test
300 g/Hectare Active Ingredient
Velvetleaf
4 Days after Application

| Formulation | % Injury |
|---|---|
| Oxyfluorfen DG Example 2 | 40 |
| Oxyfluorfen DG Example 4 | 45 |
| Oxyfluorfen DG Example 5 | 50 |
| Oxyfluorfen Emulsifiable Concentrate (1.6 E) | 90 |
| Untreated | 0 |
| Oxyfluorfen 25 WP | 80 |
| Oxyfluorfen Emulsifiable Concentrate (1.6 E) | 100 |
| Untreated | 0 |

Although the invention has been described in regard to its preferred embodiments, which constitute the best mode presently known to the inventors, it should be understood that various changes and modifications as would be obvious to one having ordinary skill in this art may be made without departing from the scope of the invention which is defined in the claims.

We claim:

1. A dispersible oxyfluorfen granule comprising: from about 10 percent to about 90 percent by weight oxyfluorfen, the oxyfluofen particles having an initial diameter of from about 3 microns to about 15 microns; from 90 percent to 10 percent by weight of at least one material selected from the group consisting of dispersants, wetting agents, disintegrants, flow aids and defoaming agents; and optionally from about 0.1 percent to about 25 percent by weight of one or more surfactants;

said oxyfluorfen granule having a particle size of at least 0.1 mm and a suspensibility of at least 70 percent and providing a reduction of at least 30 percent in vapor injury to desirable plants as compared to conventional oxyfluorfen formulations.

2. The dispersible oxyfluorfen granule of claim 1 comprising at least 65 percent oxyfluorfen.

3. The dispersible oxyfluorfen granule of claim 1 comprising at least 80 percent oxyfluorfen.

4. The dispersible granule of claim 1 wherein said dispersant is a sulfonated lignin.

5. The dispersible granule of claim 1 wherein said flow aid is a silica compound.

6. The dispersible granule of claim 1 wherein said wetting agent is a naphthalene sulfonate.

7. The dispersible granule of claim 1 wherein said defoaming agent is a silicone or silica compound.

8. The dispersible granule of claim 1 wherein said dispersant is Reax® 85A or Morwet® D 425.

9. The dispersible granule of claim 1 wherein said flow aid is HiSil® 233.

10. The dispersible granule of claim 1 wherein said wetting agent is Morwet® B or Triton® XN-45S.

11. The dispersible granule of claim 1 wherein said defoaming agent is Mazu® DF-1300.

12. A process of producing an oxyfluorfen dispersible granule of claim 1 comprising:
   a) combining a flow aid with oxyfluorfen and milling to a particle size of less than 20 microns;
   b) adding less than 25 percent by weight water and a dispersant to the product of step (a) and mixing until a paste is obtained;
   c) granulating said paste to produce granules; and
   d) drying said granules.

13. The process of claim 12 further comprising:
   a) milling a mixture of oxyfluorfen and flow aid to a particle size between 3 and 15 microns;
   b) adding a dispersant and 18–25 percent by weight water to the milled mixture of step (a) and mixing until a homogeneous, extrudable paste is obtained;
   c) extruding said paste to form granules; and
   d) drying said extruded granules at a temperature of less than 60° C. to a moisture content of less than 2% by weight.

14. A method for preventing vapor injury to desirable plants when applying oxyfluorfen for control of undesirable plant growth, comprising applying to the locus of the undesirable plant growth a suspension of oxyfluorfen granules having a particle size of at least 0.1 mm and a suspensibility of at least 70 percent and comprising: from about 10 percent to about 90 percent by weight oxyfluorfen particles having a diameter of from about 3 microns to about 15 microns; from 90 percent to 10 percent by weight of at least one material selected from the group consisting of dispersants, wetting agents, disintegrants, flow aids and defoaming agents; and optionally from about 0.1 percent to about 25 percent by weight of one or more surfactants; said method providing a reduction of at least 30 percent in vapor injury to desirable plants as compared to conventional oxyfluorfen formulations.

15. The method according to claim 14, wherein the process of milling is conducted in the presence of a flow aid.

16. The method according to claim 14, wherein the process of agglomerating the paste is accomplished by extrusion.

17. The method according to claim 14, wherein the oxyfluorfen is milled to particle size from about 3 to about 15 microns.

18. The method according to claim 14, wherein from 18% to about 25% of water, based on the total weight of the ingredients, is added to the milled oxyfluorfen.

19. The method according to claim 14, wherein the agglomerated dispersible oxyfluorfen particles are dried to a moisture content of less than 2% by weight.

20. The method according to claim 14, wherein said dispersible oxyfluorfen particles contain at least 65% oxyfluorfen.

21. The method according to claim 14, wherein said dispersible oxyfluorfen particles contain at least 80% oxyfluorfen.

* * * * *